United States Patent

Stindl et al.

Patent Number: 5,432,170
Date of Patent: Jul. 11, 1995

[54] PROCESS FOR THE PRODUCTION OF SEMISOLID PREPARATIONS CONTAINING MICRONIZED ACTIVE INGREDIENTS

[75] Inventors: Wolfgang Stindl, Eisenstadt; Erich Leitner, Vienna, both of Austria; Johannes Tack; Erwin Dargel, both of Berlin, Germany

[73] Assignee: Schering Aktiengesellschaft, Berlin and Bergkamen, Germany

[21] Appl. No.: 66,077

[22] PCT Filed: Jul. 16, 1991

[86] PCT No.: PCT/DE91/00593

§ 371 Date: May 17, 1993

§ 102(e) Date: May 17, 1993

[87] PCT Pub. No.: WO93/01836

PCT Pub. Date: Feb. 4, 1993

[51] Int. Cl.⁶ .............. A61K 47/00; A61K 47/26; A61K 47/14

[52] U.S. Cl. .............. 514/179; 514/180; 514/969; 514/975; 514/29; 514/152; 514/159; 514/420; 514/785

[58] Field of Search .............. 514/179, 180, 969, 975; 424/85.8

[56] References Cited

U.S. PATENT DOCUMENTS

| | | | |
|---|---|---|---|
| 3,892,857 | 7/1975 | Difazio et al. | 514/863 |
| 4,284,630 | 8/1981 | Yu et al. | 514/179 |
| 4,391,755 | 7/1983 | Wang et al. | 514/179 |
| 4,447,426 | 5/1984 | Wang et al. | 514/179 |
| 4,797,402 | 1/1989 | Dorsey | 514/171 |
| 4,859,659 | 8/1989 | Bittler et al. | 514/177 |
| 4,868,168 | 9/1989 | O'Laughlin et al. | 514/179 |
| 4,868,169 | 9/1989 | O'Laughlin et al. | 514/179 |
| 4,883,792 | 11/1989 | Timmins et al. | 514/179 |
| 4,894,237 | 1/1990 | Bellani et al. | 424/486 |
| 4,918,065 | 4/1990 | Stindl et al. | 514/179 |

FOREIGN PATENT DOCUMENTS 2207692 6/1974 France.
4012514 10/1991 Germany.

*Primary Examiner*—Ronald W. Griffin
*Attorney, Agent, or Firm*—Millen, White, Zelano, & Branigan

[57] ABSTRACT

A process for the production of semisolid preparations containing micronized active ingredients is described which is characterized in that a mixture of one or two nonionic surfactants with an HLB of 9 to 18 with 2.3 to 100 times the amount by weight of a fatty acid ester of general formula $$R_1—COO—R_2$$

in which $R_1$ and $R_2$ each represent alkyl groups or alkenyl groups with (12) to (32) carbon atoms, or a mixture of these fatty acid esters is heated until it melts, the melt with stirring is put into (10) to (200) times the amount by weight of a semisolid preparation, which is heated approximately to the same temperature, the mixture is allowed to cool with stirring and mixed with the micronized active ingredient or active ingredient mixture as well as optionally with scents.

17 Claims, No Drawings

PROCESS FOR THE PRODUCTION OF SEMISOLID PREPARATIONS CONTAINING MICRONIZED ACTIVE INGREDIENTS

The invention relates to a process for the production of semisolid preparations containing micronized active ingredients, characterized in that a mixture of one or two nonionic surfactants with an HLB of 9 to 18 with 2.3 to 100 times the amount by weight of a fatty acid ester of general formula $$R_1\text{—COO—}R_2$$

in which $R_1$ and $R_2$ each represent alkyl groups or alkenyl groups with 12 to 32 carbon atoms, or of a mixture of these fatty acid esters is heated until it melts, the melt with stirring is put into 10 to 200 times the amount by weight of a semisolid preparation, which is heated approximately to the same temperature, the mixture is allowed to cool with stirring and mixed with the micronized active ingredient or active ingredient mixture as well as optionally with scents.

The semisolid preparations produced according to the process of the invention make possible a better availability of the active ingredient or active ingredient mixture than the semisolid formulations containing micronized active ingredients produced in a conventional way. This has the result that the preparations according to the invention require significantly lower active ingredient concentrations to show the same effectiveness than the formulations produced in the conventional way.

The actual substance mixture promoting the availability (designated below as "substance mixture") is a mixture of one or two nonionic surfactants with an HLB of 9 to 18 and 2.3 to 100 times the amount by weight (especially 2.4 to 30 times the amount by weight) of a fatty acid ester of general formula $$R_1\text{—COO—}R_2$$

in which $R_1$ and $R_2$ are the same or different and each represent an alkyl group or an alkenyl group with 12 to 32 carbon atoms or a mixture of these fatty acid esters.

Nonionic surfactants, which are suitable for the production of the "substance mixture," are described, for example, in Ullmanns Enzyklopädie der technischen Chemie [Ullmann's Encyclopedia of Industrial Chemistry], 4th Edition, Volume 22 (Verlag Chemie; DE-Weinheim et al., 1982, pp. 488–496) and 1983 in "International McCutcheon's Emulsifiers/Detergents/Functional Materials" (Glen Rock N.J. 07452; USA).

Suitable surfactants are in particular ethoxylates soluble in water and insoluble in paraffin oil and within them preferably ethoxylates, which are terminally blocked.

Such surfactants are, for example:
Polysorbate 60 (manufacturer: ICI)
PEG-2000-stearate (manufacturer: ICI)
PEG-400-stearate (manufacturer: BASF)
Pluronic  P103 (Products Chimiques Ugine-Kuhlmann [Ugine-Kuhlmann Chemical Products])
Arlatone ®T (Atlas Chemical Industries, N.V.)
Tween ®21 (Atlas Chemical Industries, N.V.) and
Myrj ®51 (Atlas Chemical Industries, N.V.)

If a mixture of 2 surfactants is used for the production of the "substance mixture," this mixture has to have an HLB of 9 to 18, but the individual components can have a lower or higher HLB. Suitable surfactant mixtures are, for example, those which in addition to the above-mentioned ethoxylates, also contain fatty acid esters of polyhydroxy compounds (such as glycerol, sorbitol, saccharose or pentaerythritol).

A fatty acid ester is, for example, the pentaerythritol monostearate.

Fatty acid esters of the already mentioned formula $$R_1\text{—COO—}R_2,$$

which are suitable for the production of the "substance mixture," are preferably those which have a total of 28 to 58 carbon atoms and especially those which have 32 to 48 carbon atoms.

Such fatty acid esters are, for example, the octadecanoic acid-octadecenyl ester, the hexadecanoic acid-eicosyl ester, the octadecanoic acid-octadecyl ester, the eicosenoic acid-docosenyl ester, the 13-docosenoic acid eicosyl ester, the 9-octadecenoic acid-tetracosyl ester, the 12-triacontenoic acid-dodecyl ester, the eicosanoic acid-docosyl ester, the octadecanoic acid-tetracosyl ester and the 10-octacosenoic acid-eicosyl ester.

For the production of the "substance mixture," the surfactant or a mixture of two surfactants is mixed with 2.3 to 100 times the amount by weight—preferably with 24 to 30 times the amount by weight—of the fatty acid ester or fatty acid ester mixture and the mixture is heated with stirring until it melts. The melting temperature depends, of course, on the selection of the components and their quantitative ratio and is normally at about 40° C. to 70° C.

The melt of the "substance mixture" is then introduced with stirring in 10 to 200 times the amount by weight—preferably 20 to 120 times the amount by weight—of a semisolid preparation, which was heated approximately to the same temperature (±about 5° C.) as the "substance mixture" itself. The semisolid preparation used for this purpose can be produced in a conventional way as O/W emulsion or mixed emulsion and is used in a more advantageous way as freshly prepared formulation for performing the process according to the invention. Suitable mixed emulsions are, for example, the double emulsion described in EP-A 0065929 if these emulsions are used; but in this case, care has been taken that low-melting releasing mixtures are used, since these double emulsions can be partially separated at temperatures above 40° C. Then, the semisolid preparation is allowed to cool to room temperature, it is mixed with the active ingredient or active ingredient mixture micronized to at most 80 my as well as optionally in addition with scents and stirred, until these components are uniformly distributed in the preparation.

Active ingredients, which are suitable for the production of semisolid preparations according to the invention, are preferably those which at room temperature are poorly soluble in water (at most about 1 percent by weight) to practically insoluble. Preferably, those active ingredients are used which can also be used in a conventional way for the production of semisolid preparations for the topical treatment of diseases of the skin. Such active ingredients are, for example:

Antibiotics such as erythromycin, chloramphenicol, tetracycline or chlorotetracycline, antiseptics such as salicylic acid, acne agents such as tretinoin, nonsteroidal antiphlogistic agents such as crotamiton, bufexamac or indomethacin and especially corticoids such as betamethasone, beclomethasone, chlorocortolone, difluorocortolone, flumethasone, fluocinolone acetamide, fluocortin butyl, fluocortolone, hydrocortisone, 6α-methyl hydrocortisone, 6α-methylprednisolone, prednicarbate, triamcinolone, triamcinolone acetamide and esters of these corticoids.

It has already been mentioned that the active ingredients in micronized form of at most 80 mμ are used. The micronized active ingredients preferably have a grain size of about 5 mμ to 40 mμ. The optimal active ingredient concentration is a function, i.a., of the type of active ingredient used and has to be determined in the individual case.

Scents, which can optionally be incorporated in the semisolid preparations according to the invention, are, for example, those of the Crematest ® series of the DRAGOCO company.

The following embodiments are used for a more detailed explanation of the invention.

Example 1

A mixture of 3.5 g of PEG-400-stearate, 7.5 g of Rewomul MG ® (manufacturer REWO Chem. Werke GmbH; DE-6497 Steinau 1), 2.0 g of cetylstearyl alcohol, 6.5 g of octyldodecanol, 12.0 g of white vaseline and 4.0 g of Mygliol ® 812 (manufacturer Hüls AG) is heated to 70° C. Then, the resulting melt is mixed with vigorous stirring with a mixture, heated to 70° C. of 15.0 g of hydrous polyacrylate gel (DAB 9), 0.2 g of sodium cetyl sulfate, 3.0 g of cera liquida, 5.0 g of 85% glycerol, 1.0 g of benzyl alcohol and 38.65 g of bidistilled water, the mixture is allowed to cool to 55° C. and it is mixed with vigorous stirring with a 55° C. "substance mixture" of 0.1 g of pentaerythritol monooleate, 0.3 g of PEG-400-stearate and 1.0 g of eicosenoic acid eicosene ester. The emulsion is allowed to cool with stirring to room temperature and it is mixed with 0.25 g of micronized 6α-fluoro-11β21-dihydroxy-16α-methyl-1,4-pregnadiene-3,20-dione and stirred until it is homogeneously distributed.

The formed semisolid preparation shows the same effectiveness on the patient as a 0.5% 6α-fluoro-,11β,21-dihydroxy-16α-methyl-1,4-pregnadiene -3,20-dione preparation in a conventional ointment preparation.

Example 2

A mixture of 10.0 g of cetylstearyl alcohol, 25.0 g of white vaseline and 1.0 g of cera liquida is heated to 70° C. Then, a 70° C. mixture of 5.0 g of polysorbate 60, 6.0 g of 85% glycerol, 1.0 g of benzyl alcohol and 5.65 g of bidistilled water is added with vigorous stirring and the semisolid preparation is allowed to cool with stirring to 50° C. The mixture is now mixed with vigorous stirring with a 50° C. "substance mixture" of 0.1 g of pentaerythritol monooleate, 0.1 g of polysorbate 60 and 0.75 g of eicosenoic acid docosene ester, it is allowed to cool to room temperature and 0.5 g of micronized D-(−)-treo-2-dichloro-N(β-hydroxy-α-hydroxymethyl) -p-nitrophenylethyl)-acetamide is distributed in it homogeneously.

Example 3

A mixture of 4.0 g of glycerol monostearate, 4.0 g of cera liquida, 4.0 g of cetanol, 6.5 g of Mygliol ® 812 (manufacturer Hüls AG) and 25 g of white vaseline are heated to 70° C. and with vigorous stirring mixed with a 70° C. mixture of 7.0 g of polyethylene glycerol monostearate, 2.9 g of propylene glycol, 1.0 g of benzyl alcohol and 38.0 g of water. The mixture is allowed to cool to 52° C. and it is mixed with vigorous stirring with a 52° C. "substance mixture" of 0.1 g of pentaerythritol monostearate, 0.5 g of PEG-2000-stearate and 4.0 g of docosenoic acid eicosenoid. The semisolid preparation is allowed to cool to room temperature and 3.0 g of micronized 1-(4-chlorobenzoyl)-5-methoxy-2-methyl-indol-3-yl-acetic acid is distributed in it homogeneously.

We claim:

1. A process for the production of a micronized active ingredient-containing semi-solid preparation, comprising heating until it melts a mixture of one or two non-ionic surfactants with an HLB of 9 to 18, with 2.3 to 100 times the amount by weight of a fatty acid ester of the formula $R_1$—COO—$R_2$, wherein $R_1$ and $R_2$ each independently are a $C_{12-32}$-alkyl or -alkenyl group, or a mixture of said fatty acid esters;

putting said melt with stirring into 10 to 100 times the amount by weight of a semi-solid preparation heated to approximately the same temperature as said melt;

cooling the resultant product with stirring; and mixing into the cooled product a micronized active ingredient or active ingredient mixture, and optionally a scent.

2. A process of claim 1, wherein the semi-solid preparation to which the melt is added is an oil-in-water emulsion or a mixed emulsion.

3. A process of claim 1, wherein the non-ionic surfactant is an ethoxylate soluble in water and insoluble in paraffin oil.

4. A process of claim 2, wherein the non-ionic surfactant is an ethoxylate soluble in water and insoluble in paraffin oil.

5. A process of claim 1, wherein the active ingredient is an antibiotic, a non-steroidal antiphlogistic agent or a corticoid.

6. A process of claim 2, wherein the active ingredient is an antibiotic, a non-steroidal antiphlogistic agent or a corticoid.

7. A process of claim 3, wherein the active ingredient is an antibiotic, a non-steroidal antiphlogistic agent or a corticoid.

8. A process of claim 4, wherein the active ingredient is an antibiotic, a non-steroidal antiphlogistic agent or a corticoid.

9. A micronized active ingredient-containing semi-solid preparation prepared by a process of claim 1.

10. A micronized active ingredient-containing semi-solid preparation prepared by a process of claim 2.

11. A micronized active ingredient-containing semi-solid preparation prepared by a process of claim 3.

12. A micronized active ingredient-containing semi-solid preparation prepared by a process of claim 9.

13. A micronized active ingredient-containing semi-solid preparation prepared by a process of claim 10.

14. A micronized active ingredient-containing semi-solid preparation prepared by a process of claim 11.

15. A micronized active ingredient-containing semi-solid preparation prepared by a process of claim 12.

16. A micronized active ingredient-containing semi-solid preparation prepared by a process of claim 13.

17. A micronized active ingredient-containing semi-solid preparation prepared by a process of claim 1, wherein the micronized active ingredient has a grain size of at most 80 mμ.

* * * * *